United States Patent [19]

Furukawa et al.

[11] 4,258,318
[45] * Mar. 24, 1981

[54] FLAW DETECTOR FOR PIPE EMPLOYING MAGNETS LOCATED OUTSIDE THE PIPE AND DETECTOR MOUNTED INSIDE AND MOVABLE ALONG THE PIPE WITH THE MAGNETS

[75] Inventors: Yasuyuki Furukawa; Yoshihisa Fujii; Hitoshi Tanaka, all of Wakayama; Tetsuya Hirota, Amagasaki, all of Japan

[73] Assignee: Sumitomo Kinzoku Kogyo Kabushiki Kaisha, Osaka, Japan

[*] Notice: The portion of the term of this patent subsequent to Dec. 20, 1994, has been disclaimed.

[21] Appl. No.: 969,125

[22] Filed: Dec. 13, 1978

Related U.S. Application Data

[63] Continuation of Ser. No. 809,829, Jun. 24, 1977, abandoned.

[51] Int. Cl.³ .................. G01R 33/12; G01N 27/82
[52] U.S. Cl. .................................. 324/220; 324/242
[58] Field of Search .......................... 324/219–221, 324/226, 227, 228, 241, 242

[56] References Cited

U.S. PATENT DOCUMENTS

| | | |
|---|---|---|
| 1,978,252 | 10/1934 | Drake .................... 324/241 |
| 2,308,159 | 1/1943 | Drummand et al. .............. 324/220 |
| 2,563,254 | 8/1951 | Lewis ....................... 324/229 |
| 3,209,243 | 9/1965 | Walters et al. ............... 324/220 |
| 3,535,623 | 10/1970 | Wood et al. .................. 324/220 |
| 3,693,075 | 9/1972 | Förester ..................... 324/220 |
| 3,872,378 | 3/1975 | Shirana et al. ............... 324/226 |

FOREIGN PATENT DOCUMENTS 2244159 5/1972 Fed. Rep. of Germany .

OTHER PUBLICATIONS

M. Karasek, "Large Signal Analysis of the Silicon pnp-Baritt Diode", 1976, Solid State Electronics, vol. 19, pp. 625–631.

Primary Examiner—Gerard R. Strecker
Assistant Examiner—Walter E. Snow
Attorney, Agent, or Firm—Ladas & Parry

[57] ABSTRACT

A detector for magnetically detecting flaws on the inner surface of a pipe of magnetizable material comprising a magnetizing assembly having exciting magnets and movable longitudinally along the exterior of the pipe and a detecting assembly movable longitudinally along the interior of the pipe. The magnetizing and detecting assemblies are opposite and close to each other through the wall of the pipe and movable longitudinally of the pipe in a synchronized manner to ensure highly accurate flaw detection.

2 Claims, 5 Drawing Figures

FLAW DETECTOR FOR PIPE EMPLOYING MAGNETS LOCATED OUTSIDE THE PIPE AND DETECTOR MOUNTED INSIDE AND MOVABLE ALONG THE PIPE WITH THE MAGNETS

This is a continuation of Application Ser. No. 809,829 filed June 24, 1977 and now abandoned.

BACKGROUND OF THE INVENTION

This invention relates to a magnetic inspection method or magnetic flaw detecting method and an apparatus therefor, and more particularly to a method and an apparatus for detecting flaws present on or in the inner surface of a steel pipe having a small diameter and a considerable length.

The inventors have developed a magnetic inspection apparatus for detecting flaws present on the outer surface of slub or round steel, or flaws present on the outer or inner surface of a steel pipe, and filed many patent and utility model applications therefor.

The principle of these apparatuses in such that a strong magnetic field is produced on a surface to be inspected, by an exciting magnet, and the magnetism-sensitive element is placed in the magnetic field thus produced for detecting a magnetic flux leaking from the position of a flaw present on the surface of a material to be inspected.

The methods for detecting flaws in the inner surface of a steel pipe are classified into two types, i.e., one, in which a head incorporating an exciting magnet mechanism and a detecting mechanism therein is inserted into a pipe along the inner surface of the pipe, and another, in which the head similar thereto is moved along the outer surface of the pipe. These prior art methods or apparatuses can not avoid more or less shortcomings. In other word, the former dictates the insertion of a head into a pipe, thus finding applications only for pipes of a large diameter (over 300 mm in inner diameter), while the latter may be applied to the inspection for pipes having relatively small diameters, while suffering from poor detecting capability.

SUMMARY OF THE INVENTION

It is accordingly a principal object of the present invention to provide a magnetic inspection method, which is applicable to pipes having small diameters, and yet provides excellent capability for detecting flaws present on or in the inner surface of a pipe.

It is another object of the present invention to provide a magnetic inspection apparatus which is applicable to pipes of relatively small diameters and provides excellent detecting capability for flaws present on or in the inner surface of a pipe.

It is a yet further object of the present invention to provide a magnetic inspection apparatus which provides ease of insertion of a detecting mechanism portion into a pipe for detecting flaws present on or in the inner surface of a pipe.

It is a yet further object of the present invention to provide a magnetic inspection apparatus, in which a magnetism-sensitive element in a detecting mechanism portion may be brought close to the inner surface of a pipe with ease, and the magnetism-sensitive element may be supported in a stable manner for detecting flaws present on or in the inner surface of a pipe.

It is a yet further object of the present invention to provide a magnetic inspection apparatus, in which a detecting mechanism portion is supported within a pipe in a stable manner, and may be freely moved or run for detecting flaws present on or in the inner surface of a pipe.

It is a further object of the present invention to provide a magnetic inspection apparatus, in which a detecting mechanism portion is operated in full synchronism with an exciting mechanism portion for detecting flaws present on or in the inner surface of a pipe.

It is a further object of the present invention to provide a magnetic inspection apparatus, in which an exciting head in an exciting mechanism portion is brought close to the magnetism-sensitive element through the medium of a wall of a pipe, while the exciting mechanism portion may be supported relative to the outer surface of the pipe in a stable manner, and smoothly run along the outer surface of the pipe for detecting flaws present in or on the inner surface of the pipe.

According to the present invention, there is provided a magnetic inspection method comprising the steps of: inserting a detecting mechanism portion incorporating a magnetism-sensitive element into a rotating pipe along the inner surface thereof; holding and shifting an exciting mechanism portion having an exciting magnet along the outer surface of a pipe, in synchronism with the detecting mechanism portion along the length of the pipe.

According to the present invention, there is provided a magnetic inspection apparatus comprising: a detecting mechanism portion including a magnetism-sensitive element built in the tip portion of a supporting rod secured to a wheeled overhead carriage member which may travel along a rail; a guide mechanism portion for guiding the supporting rod with the tip of the supporting rod being supported by the inner surface of a pipe; and an exciting mechanism portion positioned in opposed relation to the detecting mechanism portion and including an exciting magnet which may travel along the rail, along with the aforesaid wheeled carriage member.

These and other features and object of the present invention will be apparent from a reading from the ensuing part of the present invention in conjunction with the accompanying drawings which indicate embodiments of the invention.

DESCRIPTION OF THE PREFERRED EMBODIMENTS

Figure 1:
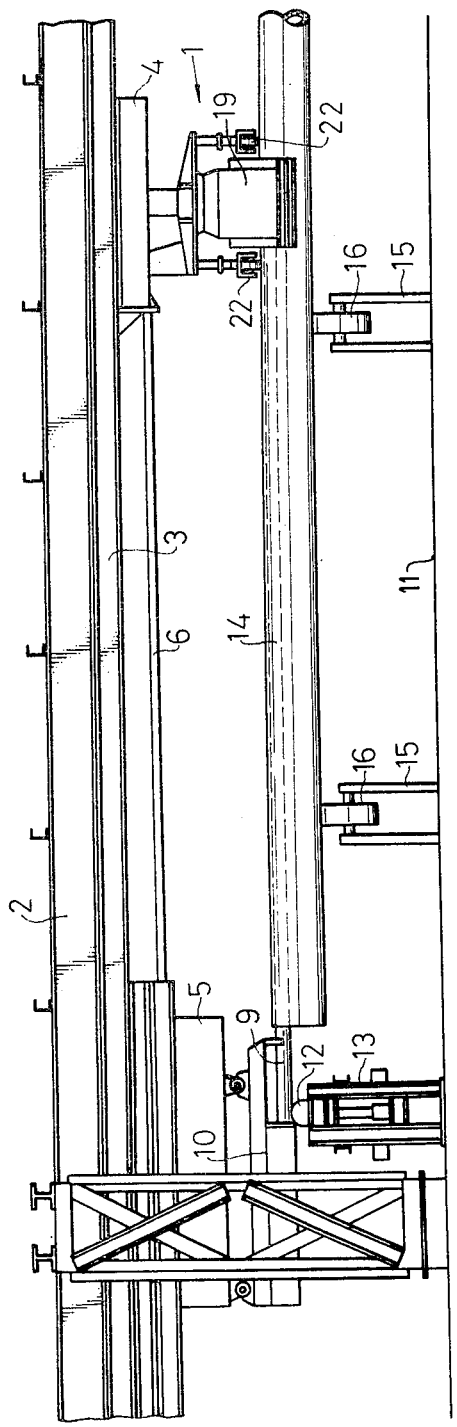
FIG. 1 is a side view of one embodiment of a magnetic inspection apparatus for detecting flaws present on or in the inner surface of a pipe according to the present invention.
Figure 2:
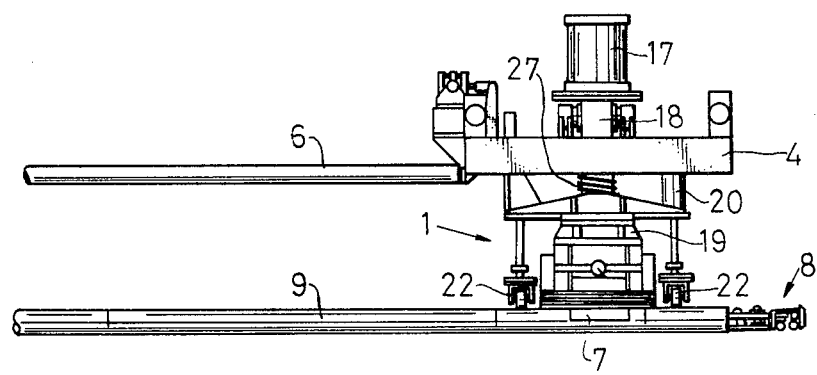
FIG. 2 is a side view showing an exciting mechanism portion and a tip portion of the supporting rod.
Figure 3:
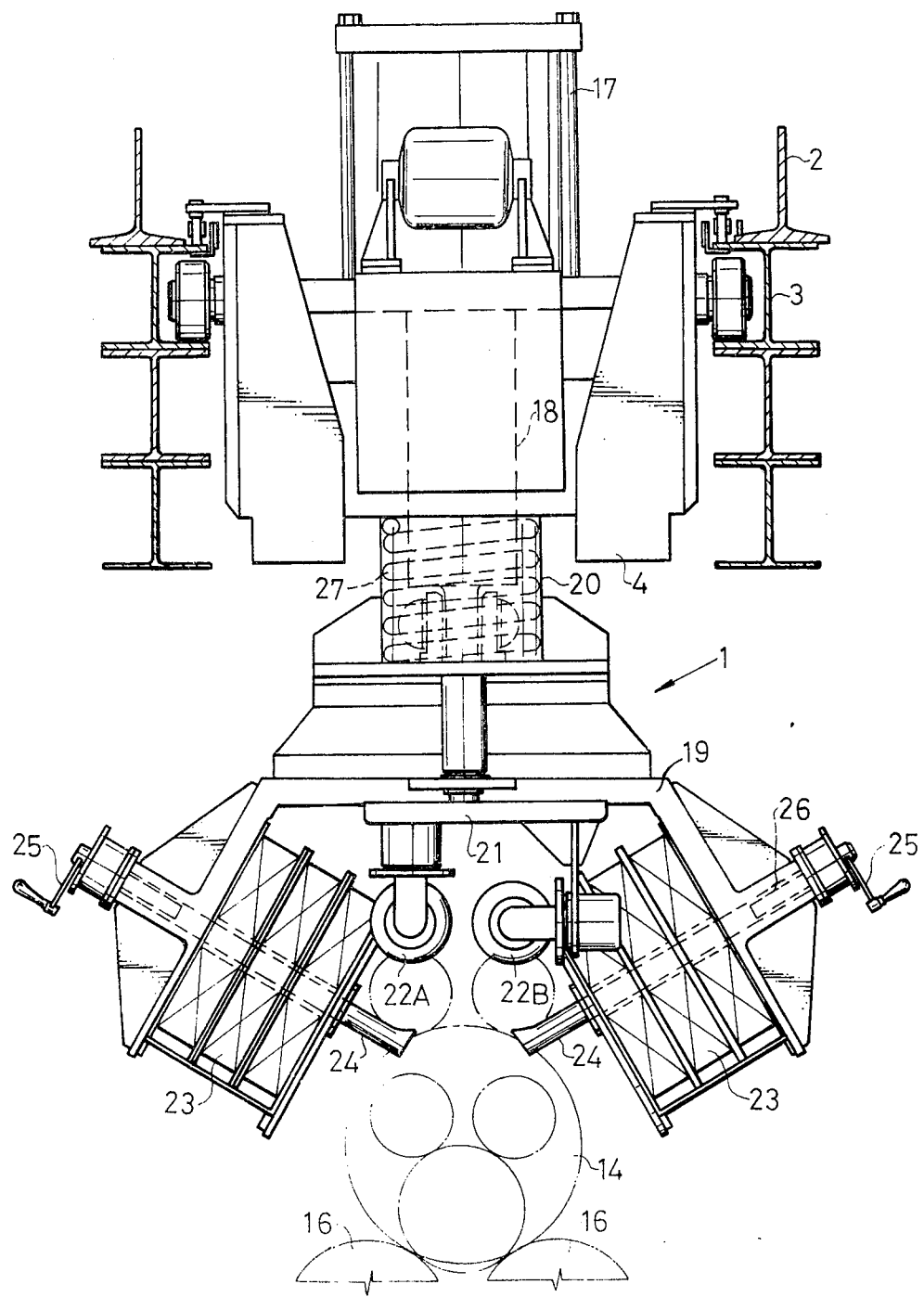
FIG. 3 is an enlarged front view showing an exciting mechanism portion.

FIGS. 1 and 2 show an outline of a magnetic inspection apparatus for detecting flaws present on or in the inner surface of a pipe according to the present invention. An exciting mechanism portion 1 travels along the outer surface of a pipe, while a detecting mechanism portion 7 is built in a tip portion of a supporting rod inserted in the pipe. In addition, the exciting mechanism portion 1 and detecting mechanism portion 7 are operably coupled through the medium of a connecting rod 6 in synchronism with each other. The exciting mechanism portion 1 is supported from a wheeled overhead carriage means 4 adapted to travel along a rail 3 secured to a beam of frame 2. In addition, the wheeled carriage means 4 is coupled through the medium of a connecting rod 6 to a wheeled overhead carriage means 5 adapted to travel along the rail 3 and positioned rearwardly of the wheeled carriage means 4. A supporting portion 10 is removably suspended from the wheeled carriage means 5 and formed with a supporting rod 9 having a detecting mechanism portion 7 and guide mechanism portion 8 at the tip thereof.

Positioned on a floor immediately under the rail 3 is a support 13 having a roller 12 on its top, with the supporting rod 9 being supported on the roller 12 in a manner to travel therealong.

A steel pipe 14 to be inspected is supported on rollers 16 which are rotatably driven and supported on the top portions of supports 15 provided on the floor 11 immediately under the rail 3. Thus the detecting mechanism portion 7 and guide mechanism portion 8, along with the supporting rod 9, are inserted into a steel pipe which is being rotated on the rollers 16, while the exciting mechanism portion 1 travels along the outer surface of the pipe, so that the inner surface of the pipe may be closely detected for flaws following a spiral pattern.

Meanwhile, the wheeled carriage means 4, 5 are coupled to a chain or cable which is driven by a motor or the like and adapted to travel along the rails 3.

The exciting mechanism portion 1 includes: an exciting head 19 pivoted to the tip portion of a suspension shaft 18 which may be vertically movable by means of a cylinder 17 mounted on the wheeled carriage means 4; and follower rollers 22A, 22B mounted on a base plate 21 which may be moved vertically by means of a cylinder 20 which in turn is mounted on the exciting head 19. The exciting head 19 includes a pair of exciting magnets 24 extending through exciting coil 23, respectively, following a V-shaped pattern by being positioned in symmetric relation to an inspecting position of a steel pipe 14. In addition, the exciting magnets 24 have their rear end portions threaded into a threaded shaft 26 adapted to be turned by means of a handle 25, so that the magnet 24 may slide for positional adjustment in the axial direction due to the rotation of the handle 25.

The follower rollers 22A, 22B may be turned about their supporting shafts so as to accommodate themselves to spiral feeding of the pipe 14 at any pitch, while one of the rollers 22A, 22B is directed in the vertical direction, and the other is directed in the horizontal direction.

Positioned in surrounding relation to the suspension shaft 18 is a spring 27 for providing a damping action to the steel pipe 14, when the rollers 22A, 22B contact the steel pipe 14. Alternatively, if the cylinder 17 is so designed as to provide an air cushion, then the spring 27 may be eliminated.

The exciting coil 23 is D.C. excited, providing a desired magnetic permeability for the pipe 14, so that a flaw present at a depth of 5% of the wall thickness of a pipe may be detected.

The detecting mechanism portion 7 includes: a mount 28 housed within the supporting rod 9; two or more attaching members 30 mounted on the mount 28 in parallel relation along the axis of the supporting rod 9, while detecting portions 29 incorporating magnetism-sensitive elements therein are attached to the tips of the attaching members 30, respectively; and guide rollers 31A, 31B attached to the mount 28 in the forward and rearward positions thereof and pivotally moved about each supporting shaft. A window 32 is provided in that portion of the supporting rod 9 which faces the detecting portions 29, so that the detecting portions 29 face the inner surface of the steel pipe 14 through the window 32 and the window permits the detecting portions 29 to be brought close to the inner surface of the steel pipe 14, when it is desired.

The undersurface of the mount 28 is supported through the medium of springs 33A, 33B on the inner surface of the supporting rod 9 Inclined surfaces 37A, 37B are provided on the undersurface of the mount 28, and disposed under the inclined surfaces 37A, 37B of the mount 28 are rollers 40A, 40B which are supported by link arm 39 which is axially movable by means of a cylinder 38. When the link arm 39 is advanced by the cylinder 38, the rollers 40A, 40B roll under the inclined surfaces 37A, 37B, thereby lifting the mount 28 vertically so as to cause the detecting portions 29 to protrude from the window 32 and be brought into close proximity with the inner surface of the steel pipe 14. Movement of the mount 28 is guided by pins 34 which move in elongated holes 36 defined in respective brackets 35 which are formed at the inner surface of the rod 9 and project into the interior thereof.

A guide mechanism portion 8 includes; a supporting frame 43 provided on the tip portion of the supporting rod and having a spherical or frusto-conical guide head 41 at its tip and guide rollers 42A, 42B adapted to turn about the supporting shafts in its middle portion; a bracket 45 projecting from the tip of the supporting rod 9 rearwardly of the supporting frame 43 and having a guide roller 44 which may be turned about its supporting shaft, at its tip; a bellcrank 48 having its intermediate portion pivoted to the bracket 45, and one end pivoted to a tip portion of the rod 46 in the cylinder, which is positioned within the supporting rod 9; a link arm 50 having one end pivoted to the bracket 47 and the other end pivoted to the bracket 49 at the tip of the supporting rod 9, respectively, the aforesaid link arm 50 being positioned in parallel with the other end portion of the bellcrank 48.

The bracket 45 is formed with a guide 51 which projects forwardly of the guide roller 44.

Figure 4:
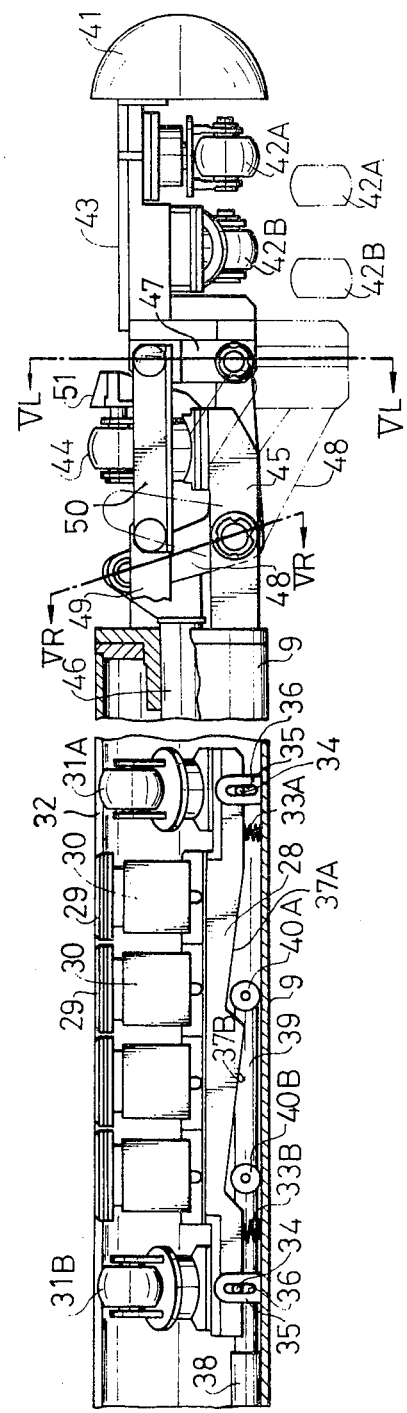
FIG. 4 is an enlarged cross-sectional view showing a detecting mechanism portion provided within a supporting rod, and a guide mechanism portion provided on the tip portion of the supporting rod.
Figure 5:
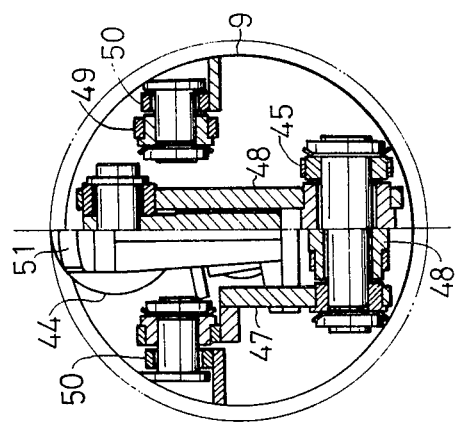
FIG. 5 is a cross sectional view, whose right hand half illustrates the right hand cross section taken along the line VR—VR of FIG. 4, and whose left hand half illustrates the left hand cross section taken along the line VL—VL of FIG. 4.

In operation, the guide mechanism portion 8 is inserted into the steel pipe 14, and then a cylinder (not shown) is actuated to extend its rod 46, to thereby rotate the bell crank 48, thus moving the supporting frame 43 towards the inner surface of the steel pipe 14, as shown by a chain line in FIG. 4 with the aid of the link arm 50. This causes the guide rollers 42A, 42B to bear against the inner surface of the pipe 14, as well as the guide roller 44 to bear against the surface of the steel pipe 14 on the opposite side thereof, so that the tip portion of the supporting rod 9 may be supported and the window 32 in the supporting rod 9 is brought close to the inner surface of the steel pipe 14.

Under this condition, when the cylinder 38 is actuated in the manner described earlier, then the mount 28 may be moved towards the inner surface of the steel pipe 14, thereby bringing the respective detecting portions 29 to the inner surface of the pipe 14.

Meanwhile, the exciting head 19 outside the steel pipe 14 is lowered to the outer surface of the steel pipe 14 by means of the cylinder 17, while the follower rollers 22A, 22B are lowered by means of the cylinder 20 to contact the surface of the steel pipe 14, thereby bringing the both poles of the exciting magnets 24 close to the outer surface of the steel pipe 14.

In this manner, the detecting portion 29 and exciting magnets 24 may be brought closer relative to each other through the medium of the steel pipe 14. In this condition, when the steel pipe 14 is rotated and the exciting mechanism portion 1 and the detecting mechanism portion 7 travel in synchronism with each other, then the inspection may be conducted for the inner surface of the steel pipe 14.

As is apparent from the foregoing description of the magnetic inspection apparatus, the detecting mechanism portion incorporating the magnetism-sensitive element therein is separated from the exciting mechanism portion having exciting magnets; the detecting mechanism portion, which is of small mass, is inserted along the inner surface of the pipe, while the exciting mechanism portion, which is of large mass, travels along the outer surface of the pipe in synchronism with the former along the length of the pipe which is being rotated. As a result, magnetic inspection is also applicable to pipes having relatively small diameters, and in addition, the exciting magnets and magnetism-sensitive elements are positioned close to each other, with the pipe being interposed therebetween, so that satisfactory magnetic permeability results, thereby permitting the positive detection of a flaw at extremely small depth.

The detecting mechanism portion 27 includes at least two detecting portions 29 which are placed side by side in relation to one another in the axial direction of the support rod 9. Therefore, each detecting portion 29 scans a different section of the interior surface of the steel pipe 14.

In addition, the detecting mechanism portion is secured to the tip portion of the supporting rod attached to a wheeled overhead carriage means which may travel along the rail, so that the detecting mechanism portion may be positively inserted into a pipe having a relatively small diameter. Still furthermore, a guide mechanism portion adapted to guide the tip portion of the supporting rod relative to the inner surface of the pipe is provided in the tip portion of the supporting rod, so that the supporting rod may be inserted into the pipe in a stable manner. Yet furthermore, the exciting mechanism portion may travel along the rail, along with the wheeled carriage means, in opposed relation to the detecting mechanism portion, so that the exciting mechanism portion may positively travel in synchronism with the detecting mechanism portion.

While the present invention has been described herein with reference to certain exemplary embodiment thereof, it should be understood that various changes, modifications, and alterations may be effected without departing from the spirit and the scope of the present invention, as defined in the appended claims.

What is claimed is:

1. A magnetic inspection apparatus for the inner surface of a pipe comprising:
   a wheeled carriage adapted to travel along a rail;
   a supporting rod having a tip portion and secured to the wheeled carriage and adapted to have its tip portion inserted into a pipe to be inspected, said supporting rod being hollow at least in the tip portion thereof and being formed in the tip portion with a window which faces the inner surface of said pipe;
   a detecting mechanism portion including; a mount housed in the tip portion of said supporting rod and movable radially thereof; at least two detecting portions placed on said mount in parallel to the axis of said supporting rod and having magnetic-sensitive elements which face the inner surface of said pipe to be inspected through said window in said supporting rod; inclined surfaces provided on the under-surface of said mount which support thereon said detecting portions and extending axially of said supporting rod, said inclined surfaces being adapted to engage rollers movable axially of said supporting rod; and two or more guide rollers mounted on said mount in parallel to each other and adapted to roll on the inner surface of said pipe to be inspected, to thereby support said mount, when said magnetic-sensitive elements are brought closer to the inner surface of said pipe to be inspected;
   a guide mechanism portion including; a supporting frame secured to the tip portion of said supporting rod and adapted to expand in a direction opposite to the direction in which said magnetic-sensitive elements project; and guide rollers attached to said supporting frame and rolling on the inner surface of said pipe, thereby supporting said supporting rod when said supporting frame in expanded;
   an exciting mechanism portion including; a DC exciting head mounted on the wheeled carriage and adapted to be brought close to the outer surface of said pipe to be inspected and to be moved away therefrom, together with said wheeled carriage, said exciting head including exciting magnets placed in opposed relation to said magnetic-sensitive elements through the medium of the wall of the pipe, and follower rollers suspending said exciting magnets and rolling on the outer surface of said pipe to be inspected, thereby supporting said exciting magnets in the vicinity of the outer surface of said pipe, respectively; and
   means for rotating the pipe to be inspected about the central axis thereof.

2. An apparatus as claimed in claim 1, wherein said supporting rod is tubular and the magnetism-sensitive elements are disposed internally of the tubular supporting rod.

* * * * *